United States Patent
Dittmer et al.

(10) Patent No.: US 11,440,834 B2
(45) Date of Patent: Sep. 13, 2022

(54) FLUORESCENT GLASS CERAMICS AND GLASSES WITH EUROPIUM CONTENT

(71) Applicant: Ivoclar Vivadent AG, Schaan (LI)

(72) Inventors: Marc Dittmer, Feldkirch (AT); Ronny Hengst, Brand-Erbisdorf (DE); Christian Ritzberger, Grabs (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 16/784,824

(22) Filed: Feb. 7, 2020

(65) Prior Publication Data

US 2020/0262739 A1 Aug. 20, 2020

(30) Foreign Application Priority Data

Feb. 14, 2019 (EP) ..................... 19157306

(51) Int. Cl.
*C03C 3/085* (2006.01)
*C03C 3/062* (2006.01)
*C03C 4/00* (2006.01)
*C03C 4/12* (2006.01)
*C03C 10/00* (2006.01)

(52) U.S. Cl.
CPC .............. *C03C 3/085* (2013.01); *C03C 3/062* (2013.01); *C03C 4/0021* (2013.01); *C03C 4/12* (2013.01); *C03C 10/0036* (2013.01); *C03C 2205/06* (2013.01)

(58) Field of Classification Search
CPC ....... C03C 3/085; C03C 3/062; C03C 4/0021; C03C 4/12; C03C 10/0036; C03C 2205/06; C03C 3/076
See application file for complete search history.

(56) References Cited

U.S. PATENT DOCUMENTS

| | | | |
|---|---|---|---|
| 5,432,130 A | 7/1995 | Rheinberger et al. | |
| 5,618,763 A | 4/1997 | Frank et al. | |
| 5,698,019 A | 12/1997 | Frank et al. | |
| 5,925,180 A | 7/1999 | Frank et al. | |
| 6,010,644 A | 1/2000 | Fu et al. | |
| 6,455,451 B1 * | 9/2002 | Brodkin | A61K 6/78 501/5 |
| 8,047,021 B2 | 11/2011 | Schweiger et al. | |
| 8,263,508 B2 | 9/2012 | Bolle et al. | |
| 8,759,237 B2 | 6/2014 | Ritzberger et al. | |
| 9,321,674 B2 | 4/2016 | Ritzberger et al. | |
| 9,402,699 B2 | 8/2016 | Ritzberger et al. | |
| 9,403,714 B2 | 8/2016 | Ritzberger et al. | |
| 9,688,567 B2 | 6/2017 | Rampf et al. | |
| 9,695,082 B2 | 7/2017 | Ritzberger et al. | |
| 9,757,311 B2 | 9/2017 | Rampf et al. | |
| 9,764,982 B2 | 9/2017 | Ritzberger et al. | |
| 9,776,912 B2 | 10/2017 | Ritzberger et al. | |
| 9,878,939 B2 | 1/2018 | Ritzberger et al. | |
| 10,131,569 B2 | 11/2018 | Krolikowski et al. | |
| 10,227,255 B2 | 3/2019 | Ritzberger et al. | |
| 10,376,343 B2 | 8/2019 | Rheinberger et al. | |
| 10,414,688 B2 | 9/2019 | Rampf et al. | |
| 10,457,589 B2 | 10/2019 | Rampf et al. | |
| 10,501,366 B2 | 12/2019 | Ritzberger et al. | |
| 2011/0256409 A1 | 10/2011 | Ritzberger et al. | |
| 2017/0119508 A1 | 5/2017 | Dittmer et al. | |
| 2018/0244563 A1 | 8/2018 | Dittmer et al. | |
| 2019/0315651 A1 | 10/2019 | Rampf et al. | |

FOREIGN PATENT DOCUMENTS

| | | | | |
|---|---|---|---|---|
| CS | 233427 B1 * | 3/1985 | ............... | C03C 4/18 |
| DE | 19647739 A1 | 3/1998 | | |
| DE | 19725552 A1 | 12/1998 | | |
| DE | 10031431 A1 | 1/2002 | | |
| DE | 102004040759 A1 * | 3/2006 | ............. | H05B 3/746 |
| DE | 102009013377 A1 | 9/2010 | | |
| EP | 0827941 A1 | 3/1998 | | |
| EP | 0916625 A1 | 5/1999 | | |
| EP | 1688398 A1 | 8/2006 | | |

OTHER PUBLICATIONS

Zhang, Yaming, et al. "Effect of Added Mullite Whisker on Properties of Lithium Aluminosilicate (LAS) Glass-Ceramics Prepared for Dental Restoration." Journal of biomedical nanotechnology 14.11 (2018): 1944-1952. (Year: 2018).*

Ozawa, Lyuji. "Emission and excitation spectra of Eu2O3 compared with Y2O3: Eu phosphor." Japanese Journal of Applied Physics 5.8 (1966): 740. (Year: 1966).*

* cited by examiner

*Primary Examiner* — Bryan D. Ripa
*Assistant Examiner* — Cameron K Miller
(74) *Attorney, Agent, or Firm* — Ann M. Knab; Thad McMurray

(57) ABSTRACT

The invention relates to glass ceramics and glasses with a europium content, containing the following components:

| Component | wt.-% |
|---|---|
| $SiO_2$ | 30.0 to 75.0 |
| $Al_2O_3$ | 10.0 to 45.0 |
| Europium, calculated as $Eu_2O_3$ | 0.05 to 5.0 | and which are suitable in particular for the production of restorations, the fluorescence properties of which largely correspond to those of natural teeth.

21 Claims, No Drawings

FLUORESCENT GLASS CERAMICS AND GLASSES WITH EUROPIUM CONTENT

CROSS-REFERENCE TO RELATED APPLICATIONS

This application claims priority to European patent application No. 19157306.2 filed on Feb. 14, 2019, the disclosure of which is incorporated herein by reference in its entirety.

FIELD OF INVENTION

The present invention relates to glass ceramics and glasses which contain europium and are suitable in particular for the production of dental restorations, the fluorescence properties of which largely correspond to those of natural teeth. The invention also relates to a process for the preparation of the glass ceramics and glasses according to the invention as well as their use as dental material and in particular for the preparation of dental restorations.

BACKGROUND

Glass ceramics are used in dentistry because of their good mechanical and optical properties in particular for the production of dental crowns and small bridges.

It is known from W. Buchalla, "Comparative Fluorescence Spectroscopy Shows Differences in Non-Cavitated Enamel Lesions", Caries Res. 2005, 39, 150-156 that, under ultraviolet light, natural teeth exhibit a bluish-white fluorescence with wavelengths in the range of from 400 to 650 nm.

Rukmani et al., J. Am. Ceram. Soc. 2007, 90, 706-711, describe the influence of V and Mn colorants on the crystallization behaviour and the optical properties of Ce-doped lithium disilicate glass ceramics. For the production of glass ceramics, a mixture of the starting materials $SiO_2$, $ZrO_2$, $Li_2CO_3$, $K_2CO_3$, $MgCO_3$ and $Al(PO_3)_3$ with $CeO_2$, $V_2O_5$ and $MnO_2$ is produced, the mixture is melted in platinum crucibles at 1500° C., cooled and then subjected to several heat treatments in a tube furnace with an air supply.

EP 0 877 071 A1 and corresponding U.S. Pat. No. 6,010,644, which is hereby incorporated by reference in its entirety, describes glasses and glass ceramics which contain inter alia $Eu^{2+}$ ions and exhibit long-lasting phosphorescence.

DE 10 2009 013 377 A1 describes the use of a borosilicate glass which is doped with $CeO_2$ or at least one oxide of another lanthanoid, inter alia $Eu_2O_3$, for increasing antiforgery security of a package by emission of electromagnetic radiation in the range between 300 and 700 nm when irradiated with UV light.

WO 2015/173230 A1 and corresponding U.S. Pat. No. 10,131,569, which is hereby incorporated by reference in its entirety, describes a method for the production of a lithium silicate glass or a lithium silicate glass ceramic, in which a melt of a starting glass which contains cerium ions is exposed to reducing conditions. $Ce^{4+}$ ions contained in the starting glass are thereby said to be completely or partially reduced to $Ce^{3+}$ ions which, because of 5d→4f transitions, exhibit a fluorescence in the wavelength range from 320 to 500 nm. A corresponding process for the production of a glass ceramic with $SiO_2$ as main crystal phase or of a glass which contains nuclei for the crystallization of $SiO_2$, is known from WO 2017/080853 A1 and corresponding U.S. Pat. No. 10,414,688, which is hereby incorporated by reference in its entirety.

However, it has been shown that the glasses and glass ceramics known from the state of the art have unsatisfactory fluorescence properties and, in particular under UV light, cannot adequately imitate the fluorescence properties of natural tooth material. In particular, the known materials do not exhibit the required fluorescence at all the relevant wavelengths in the UV range. Dental restorations produced from such glass ceramics are thereby recognizable as restorations, in particular under the influence of UV light, or are perceived as missing teeth or defects. Moreover, in the case of the glasses and glass ceramics produced in this way, considerable impairment of the fluorescence properties results through heat treatments under oxidizing conditions, for example during sintering.

SUMMARY

The object of the invention is to provide glass ceramics and glasses which, at excitation wavelengths throughout the entire relevant UV range, above all in the range of from 250 nm to 430 nm and in particular in the range of from 360 nm to 430 nm, exhibit fluorescence and are thus suitable in particular for the production of dental restorations which not only have good mechanical properties, but can also largely imitate the fluorescence properties of natural tooth material at excitation wavelengths throughout the entire relevant UV range. In particular, the glass ceramics and glasses should also be suitable as blending components for setting the fluorescence properties of other glasses and glass ceramics.

DETAILED DESCRIPTION

This object is achieved according to the invention by a glass or a glass ceramic with europium content, which comprise the following components:

| | |
|---|---|
| $SiO_2$ | 30.0 to 75.0 |
| $Al_2O_3$ | 10.0 to 45.0 |
| Europium, calculated as $Eu_2O_3$ | 0.05 to 5.0 |

It has surprisingly been shown that the glass according to the invention and the glass ceramic according to the invention exhibit improved fluorescence properties compared with the state of the art at excitation wavelengths in the range of from 250 to 430 nm and in particular also at excitation wavelengths in the range of from 360 to 430 nm and these fluorescence properties are, in addition, largely stable towards heat treatments and oxidizing conditions.

Without being limited to a specific theory, it is assumed that an equilibrium between $Eu^{2+}$ and $Eu^{3+}$ ions is formed in the glasses and glass ceramics according to the invention. Because of 5d→4f transitions, the $Eu^{2+}$ ions exhibit a fluorescence at excitation wavelengths throughout the entire range of from 250 to 430 nm which is particularly suitable for imitating the fluorescence properties of natural tooth material, in particular in the case of excitation in the UV range.

According to the invention, it is preferred that the glass and the glass ceramic comprise 32.0 to 72.0, in particular 35.0 to 65.0 and preferably 38.0 to 50.0 wt.-% $SiO_2$.

It is further preferred that the glass and the glass ceramic comprise 15.0 to 40.0, in particular 20.0 to 40.0, preferably 25.0 to 40.0 and particularly preferably 30.0 to 40.0 wt.-% $Al_2O_3$.

The glass and the glass ceramic preferably comprise 0.1 to 4.0, in particular 0.3 to 3.0, preferably 0.5 to 2.0, more preferably 0.6 to 1.0 and particularly preferably 0.65 to 0.85 wt.-% europium, calculated as $Eu_2O_3$.

It is further preferred that the glass and the glass ceramic comprise 8.0 to 30.0 wt.-%, in particular 12.0 to 29.0, preferably 15.0 to 28.0 and particularly preferably 20.0 to 27.0 wt.-% $Me^{II}O$, wherein $Me^{II}O$ is selected from MgO, CaO, SrO and/or ZnO. In a preferred embodiment, the glass and the glass ceramic comprise 8.0 to 30.0, in particular 12.0 to 29.0, preferably 15.0 to 28.0 and particularly preferably 20.0 to 27.0 wt.-% CaO and/or SrO.

Glasses and glass ceramics which comprise at least one and preferably all of the following components in the specified amounts are particularly preferred:

| Component | wt.-% |
|---|---|
| MgO | 0 to 13.0, in particular 3.5 to 13.0 |
| CaO | 0 to 22.0, in particular 5.0 to 22.0 |
| SrO | 0 to 28.0, in particular 9.0 to 28.0 |
| ZnO | 0 to 5.0, in particular 4.0 to 5.0 |

It is furthermore preferred that the glass and the glass ceramic comprise 0 to 10.0, in particular 0 to 5.0 and preferably 0 to 1.0 wt.-% BaO, and most preferably are substantially free from BaO.

In a preferred embodiment, the glass and the glass ceramic comprise 0 to 2.0, in particular 0.1 to 1.2 and preferably 0.3 to 0.7 wt.-% tin, calculated as SnO.

Preferably, the glass and the glass ceramic further comprise 0 to 5.0, preferably 0.5 to 4.0 and preferably 1.0 to 3.0 wt.-% cerium, calculated as $CeO_2$.

The glass and the glass ceramic can further comprise alkali metal oxide $Me^{I}_2O$ in an amount of from 0 to 15.0, in particular 0 to 10.0, preferably 0 to 5.0, particularly preferably 0 to 1.0 and most preferably 0 to 0.5 wt.-%, wherein this $Me^{I}_2O$ is selected in particular from $Li_2O$, $Na_2O$, $K_2O$, $Rb_2O$ and $Cs_2O$ and is preferably selected from $Li_2O$, $Na_2O$ and $K_2O$. Particularly preferably, the glass and the glass ceramic comprise at least one and in particular all of the following alkali metal oxides $Me^{I}_2O$ in the specified amounts:

| Component | wt.-% |
|---|---|
| $Li_2O$ | 0 to 5.0 |
| $Na_2O$ | 0 to 10.0 |
| $K_2O$ | 0 to 14.0 |
| $Rb_2O$ | 0 to 7.0 |
| $Cs_2O$ | 0 to 13.0 |

The glass and the glass ceramic can, furthermore, comprise 0 to 10.0, in particular 0 to 4.0 and preferably 0 to 2.5 wt.-% further oxide of trivalent elements $Me^{III}_2O_3$. The term "further oxide of trivalent elements $Me^{III}_2O_3$" denotes trivalent oxides with the exception of $B_2O_3$, $Al_2O_3$, $Eu_2O_3$ and $Ce_2O_3$, wherein this $Me^{III}_2O_3$ is selected in particular from $Y_2O_3$, $La_2O_3$, $Ga_2O_3$ and/or $In_2O_3$. Particularly preferably, the glass and the glass ceramic comprise at least one and in particular all of the following further oxides of trivalent elements $Me^{III}_2O_3$ in the specified amounts:

| Component | wt.-% |
|---|---|
| $Y_2O_3$ | 0 to 3.0 |
| $La_2O_3$ | 0 to 2.0 |
| $Ga_2CO_3$ | 0 to 2.0 |
| $In_2O_3$ | 0 to 1.0 |

It is furthermore preferred that the glass and the glass ceramic comprise 0 to 3.0, in particular 0 to 2.0 and preferably 0 to 1.0 wt.-% $B_2O_3$, and most preferably are substantially free from $B_2O_3$.

Furthermore, the glass and the glass ceramic can comprise further oxide of tetravalent elements $Me^{IV}O_2$ in an amount of 0 to 15.0, in particular 0 to 4.0 and particularly preferably 0 to 2.5 wt.-%. The term "further oxide of tetravalent elements $Me^{IV}O_2$" denotes tetravalent oxides with the exception of $SiO_2$, $SnO_2$, $CeO_2$ and $TiO_2$, wherein this $Me^{IV}O_2$ is selected in particular from $ZrO_2$ and/or $GeO_2$. Particularly preferably, the glass and the glass ceramic comprise at least one and in particular all of the following further oxides of tetravalent elements $Me^{IV}O_2$ in the specified amounts:

| Component | wt.-% |
|---|---|
| $ZrO_2$ | 0 to 15.0 |
| $GeO_2$ | 0 to 5.0 |

It is furthermore preferred that the glass and the glass ceramic comprise 0 to 5.0, in particular 0 to 2.5 and preferably 0 to 1.0 wt.-% $TiO_2$ and most preferably is substantially free from $TiO_2$.

Moreover, the glass and the glass ceramic can comprise oxide of pentavalent elements $Me^{V}_2O_5$ in an amount of 0 to 6.0 and in particular 0 to 5.0 wt.-%, wherein this $Me^{V}_2O_5$ is selected in particular from $P_2O_5$, $V_2O_5$, $Ta_2O_5$ and/or $Nb_2O_5$. Particularly preferably, the glass and the glass ceramic comprise at least one and in particular all of the following further oxides of pentavalent elements $Me^{V}_2O_5$ in the specified amounts:

| Component | wt.-% |
|---|---|
| $P_2O_5$ | 0 to 6.0 |
| $V_2O_5$ | 0 to 6.0 |
| $Ta_2O_5$ | 0 to 5.0 |
| $Nb_2O_5$ | 0 to 5.0 |

In addition, the glass and the glass ceramic can comprise 0 to 6.0 wt.-% oxide of hexavalent elements $Me^{VI}O_3$, wherein this $Me^{VI}O_3$ is selected in particular from $WO_3$ and/or $MoO_3$. Particularly preferably, the glass and the glass ceramic comprise at least one and in particular all of the following $Me^{VI}O_3$ oxides in the specified amounts:

| Component | wt.-% |
|---|---|
| $WO_3$ | 0 to 6.0 |
| $MoO_3$ | 0 to 5.0 |

The glass and the glass ceramic can, furthermore, comprise oxides of further f-elements, such as oxides of Pr, Nd, Gd, Tb, Dy, Er and Yb and in particular oxides of Tb and/or Dy.

Furthermore, the glass and the glass ceramic can comprise 0 to 5.0 and in particular 0 to 1.0 wt.-% fluorine.

A glass and a glass ceramic which comprise at least one and preferably all of the following components in the specified amounts are particularly preferred:

| Component | wt.-% |
| --- | --- |
| $SiO_2$ | 32.0 to 72.0 |
| $Al_2O_3$ | 15.0 to 40.0 |
| Europium, calculated as $Eu_2O_3$ | 0.1 to 4.0 |
| Cerium, calculated as $CeO_2$ | 0 to 5.0 |
| Tin, calculated as SnO | 0 to 2.0 |
| $Me^I_2O$ | 0 to 15.0 |
| $Me^{II}O$ | 0 to 30.0 |
| $Me^{III}_2O_3$ | 0 to 10.0 |
| $Me^{IV}O_2$ | 0 to 15.0 |
| $Me^V_2O_5$ | 0 to 6.0 |
| $Me^{VI}O_3$ | 0 to 6.0 |
| Fluorine | 0 to 5.0, | wherein $Me^I_2O$, $Me^{II}O$, $Me^{III}_2O_3$, $Me^{IV}O_2$, $Me^V_2O_5$ and $Me^{VI}O_3$ have in particular the meanings specified above.

In a further particularly preferred embodiment, the glass and the glass ceramic comprise at least one and preferably all of the following components in the specified amounts:

| Component | wt.-% |
| --- | --- |
| $SiO_2$ | 32.0 to 72.0 |
| $Al_2O_3$ | 15.0 to 40.0 |
| Europium, calculated as $Eu_2O_3$ | 0.1 to 4.0 |
| Cerium, calculated as $CeO_2$ | 0 to 5.0 |
| Tin, calculated as SnO | 0 to 2.0 |
| $Li_2O$ | 0 to 5.0 |
| $Na_2O$ | 0 to 10.0 |
| $K_2O$ | 0 to 14.0 |
| $Rb_2O$ | 0 to 7.0 |
| $Cs_2O$ | 0 to 13.0 |
| MgO | 0 to 13.0 |
| CaO | 0 to 22.0 |
| SrO | 0 to 28.0 |
| ZnO | 0 to 5.0 |
| BaO | 0 to 10.0 |
| $B_2O_3$ | 0 to 3.0 |
| $Y_2O_3$ | 0 to 3.0 |
| $La_2O_3$ | 0 to 2.0 |
| $Ga_2O_3$ | 0 to 2.0 |
| $In_2O_3$ | 0 to 1.0 |
| $ZrO_2$ | 0 to 15.0 |
| $GeO_2$ | 0 to 5.0 |
| $TiO_2$ | 0 to 5.0 |
| $P_2O_5$ | 0 to 6.0 |
| $V_2O_5$ | 0 to 6.0 |
| $Ta_2O_5$ | 0 to 5.0 |
| $Nb_2O_5$ | 0 to 5.0 |
| $WO_3$ | 0 to 6.0 |
| $MoO_3$ | 0 to 5.0 |
| $Dy_2O_3$ | 0 to 3.0 |
| $Tb_4O_7$ | 0 to 2.0 |
| Fluorine | 0 to 1.0. |

The glass ceramic according to the invention preferably comprises at least one aluminosilicate as crystal phase and in particular as main crystal phase. In a further preferred embodiment, the glass ceramic according to the invention comprises a calcium aluminosilicate or strontium aluminosilicate or a mixture thereof, preferably a calcium aluminosilicate or strontium aluminosilicate, as crystal phase and in particular as main crystal phase. Without being limited to a specific theory, it is assumed that in the glass ceramics according to the invention $Eu^{2+}$ ions are incorporated into the crystal lattice of the above-named crystal phases, and the fluorescence properties thereof are thereby further improved and stabilized.

The term "main crystal phase" denotes the crystal phase which has the highest proportion by mass of all the crystal phases present in the glass ceramic. The masses of the crystal phases are determined using in particular the Rietveld method. A suitable method for the quantitative analysis of the crystal phases using the Rietveld method is described e.g. in M. Dittmer's doctoral thesis "Gläser und Glaskeramiken im System MgO—$Al_2O_3$—$SiO_2$ mit $ZrO_2$ als Keimbildner" [Glasses and glass ceramics in the MgO—$Al_2O_3$—$SiO_2$ system with $ZrO_2$ as nucleating agent], University of Jena 2011.

It is further preferred that the glass ceramic according to the invention comprises at least 5 wt.-%, in particular at least 10 wt.-% and preferably at least 20 wt.-% aluminosilicate as crystal phase, in particular in the form of calcium aluminosilicate, strontium aluminosilicate or mixtures thereof.

The type and the amount of the crystal phases formed can be controlled in particular by the composition of the starting glass used, as well as the heat treatment which is used for the production of the glass ceramic from the glass. The examples illustrate this by varying the composition and the heat treatment used.

The invention likewise relates to precursors with a corresponding composition from which the glass ceramic according to the invention can be produced by heat treatment. These precursors are a glass with a corresponding composition (also referred to as starting glass) and a glass with a corresponding composition with nuclei. The term "corresponding composition" means that these precursors comprise the same components in the same amounts as the glass ceramic, wherein the components with the exception of fluorine are calculated as oxides, as is customary in the case of glasses and glass ceramics.

The invention likewise relates to a glass according to the invention which comprises nuclei for the crystallization of an aluminosilicate and in particular of calcium aluminosilicate and/or strontium aluminosilicate. Through heat treatment of the glass according to the invention, the glass with nuclei according to the invention can first be produced, which in turn can be converted through further heat treatment into the glass ceramic according to the invention, in particular with an aluminosilicate as crystal phase and preferably as main crystal phase.

The glass according to the invention is produced in particular in such a way that a mixture of suitable starting materials, such as carbonates, oxides, phosphates and fluorides, is melted at temperatures of in particular from 1500 to 1800° C., for 0.5 to 10 h, and the glass melt obtained is introduced in water in order to produce a granulate. This granulate can be pressed, after grinding, to form a blank, a so-called powder compact, or processed to form a powder.

The invention is therefore likewise directed to a process for the preparation of the glass ceramic according to the invention, in which the glass, in particular the glass with nuclei, is subjected to at least one heat treatment at a temperature of from 1000 to 1500° C., preferably 1050 to 1450° C., for a duration of in particular 10 to 720 min and preferably 30 to 120 min.

Thus, in a preferred embodiment, the invention relates to a process for the preparation of the glass ceramic according to the invention, in which
(a) powder of the glass according to the invention, optionally after the addition of further components, such as other glasses, glass ceramics and/or pressing agents, is pressed to form a powder compact, and
(b) the powder compact is subjected to a heat treatment at a temperature of from 1000 to 1500° C., preferably 1050 to 1450° C., for a duration of in particular from 10 to 720 min, preferably 30 to 120 min.

A nucleation can optionally be carried out before the heat treatment in step (b).

The melt of the starting glass can optionally be reacted with at least one reducing agent. In principle, all the agents which are able to reduce $Eu^{3+}$ ions to $Eu^{2+}$ ions under the conditions of the process come into consideration as reducing agents. Those reducing agents are preferred which can be removed from the glass melt residue-free after the reduction.

In particular, gaseous reducing agents, as well as reducing agents which, after the reduction, are burnt out from the glass melt under the conditions of the process according to the invention, are preferred. Examples of gaseous reducing agents are gases which comprise hydrogen and preferably mixtures of hydrogen and nitrogen. Furthermore, examples of reducing agents are substances which comprise at least one oxidizable carbon atom, in particular carbon, for example graphite, organic salts, carbohydrates and cereal flours.

According to a preferred embodiment, the melt of the starting glass is formed from a glass-forming composition which comprises at least one reducing agent. As the at least one reducing agent, a compound is preferred, which comprises at least one oxidizable carbon atom and is preferably selected from the group consisting of organic salts, carbohydrates and cereal flours. Acetates are examples of particularly suitable organic salts.

In a particularly preferred embodiment, a europium acetate, in particular europium(III) acetate hydrate, is used as reducing agent.

According to a further preferred embodiment, the at least one reducing agent is a reducing gas, wherein the gas preferably comprises hydrogen and preferably comprises hydrogen and nitrogen. Mixtures of hydrogen and nitrogen which comprise about 5 vol.-% hydrogen and are also referred to as forming gas are particularly suitable. The extent of the reduction can be controlled via the amount of the gas supplied and in particular via the flow rate and duration of the gas supply. Preferably, the amount of the effective component of the reducing gas, preferably hydrogen, is 0.05 to 5 l/min, in particular 0.1 to 1 l/min and preferably 0.2 to 0.5 l/min, for a duration of 10 to 180 min, in particular 20 to 120 min and preferably 30 to 90 min.

The invention further relates to a glass according to the invention and a glass ceramic according to the invention, which have a whitish-blue fluorescence in the CIE colour space.

The glasses and glass ceramics with europium content according to the invention are, in particular, suitable as blending components for adjusting the fluorescence properties of other glasses and glass ceramics. A glass or a glass ceramic comprising the glass with europium content according to the invention or the glass ceramic with europium content according to the invention, therefore represent a further subject of the invention. A glass and a glass ceramic are particularly preferred, which comprise the glass with europium content according to the invention or the glass ceramic with europium content according to the invention in an amount of from 0.1 to 50 wt.-%, in particular 0.2 to 40 wt.-%, preferably 0.5 to 30 wt.-%, particularly preferably 1 to 20 wt.-% and more preferably 5 to 10 wt.-%.

The glass with europium content according to the invention or the glass ceramic with europium content according to the invention can in particular be used as component of an inorganic-inorganic composite or in combination with a variety of other glasses and/or glass ceramics, wherein the composites or combinations can in particular be used as dental materials. Particularly preferably, the composites or combinations can be present in the form of sintered blanks. Examples of other glasses and glass ceramics for the production of inorganic-inorganic composites and of combinations are disclosed in DE 43 14 817 A1, DE 44 23 793 C1, DE 44 23 794 C1, DE 44 28 839 A1, DE 196 47 739 A1, DE 197 25 552 A1, DE 100 31 431 A1, EP 0 827 941 A1, EP 0 916 625 A1, WO 00/34196 A2, EP 1 505 041 A1, EP 1 688 398 A1, EP 2 287 122 A1, EP 2 377 831 A1, EP 2 407 439 A1, WO 2013/053863 A2, WO 2013/053864 A2, WO 2013/053865 A2, WO 2013/053866 A2, WO 2013/053867 A2, WO 2013/053868 A2, WO 2013/164256 A1, WO 2014/170168 A1, WO 2014/170170 A2, WO 2015/067643 A1, WO 2015/155038 A1, WO 2015/173394 A1, WO 2016/120146 A1, WO 2017/032745 A1 WO 2017/055010 A1 U.S. Pat. No. 10,457,589, US 2018244563, U.S. Pat. No. 8,759,237, US 2011256409, U.S. Pat. No. 10,501,366, which US patents and published applications are hereby incorporated by reference in their entirety. These glasses and glass ceramics belong to the silicate, borate, phosphate or aluminosilicate group. Preferred glasses and glass ceramics are of the $SiO_2$—$Al_2O_3$-$K_2$a type (with cubic or tetragonal leucite crystals), $SiO_2$—$B_2O_3$-$Na_2$a type, alkali-silicate type, alkali-zinc-silicate type, silico-phosphate type and/or $SiO_2$—$ZrO_2$ type. Particularly preferred are lithium-silicate glass ceramics and in particular glass ceramics which comprise lithium metasilicate or lithium disilicate as main crystal phase and optionally further crystal phases such as apatite, diopside, quartz and/or wollastonite, as well as glass ceramics which comprise $SiO_2$, in particular in the form of low quartz, as main crystal phase. By mixing such glasses or glass ceramics with the glasses and/or glass ceramics with europium content according to the invention, the fluorescence properties can in particular be set as desired.

The glass ceramics according to the invention and the glasses according to the invention, in particular in the form of composites and combinations, are present in particular in the form of powders, granulates or blanks in any shape and size, e.g. monolithic blanks, such as platelets, cuboids or cylinders, or powder compacts, in unsintered, partially sintered or densely sintered form. In these forms, they can easily be further processed, e.g. to form dental restorations. However, they can also be present in the form of dental restorations such as inlays, onlays, crowns, partial crowns, bridges, veneers, facets or abutments.

Dental restorations, such as inlays, onlays, crowns, partial crowns, bridges, veneers, facets or abutments, can be produced from the glass ceramics according to the invention and the glasses according to the invention, in particular in the form of composites and combinations. The invention therefore relates to the use thereof as dental material and in particular the use thereof for the preparation of dental restorations. It is preferred that the glass ceramic or the glass is given the shape of the desired dental restoration by pressing or machining.

The pressing is usually effected under increased pressure and at increased temperature. It is preferred that the pressing is effected at a temperature of from 700 to 1150° C. and in particular 700 to 1000° C. It is further preferred to carry out the pressing at a pressure of from 10 to 30 bar. During pressing, the desired shape change is achieved by viscous flow of the material used. The glass according to the invention and the glass with nuclei according to the invention as well as preferably the glass ceramic according to the invention can be used for the pressing. The glasses and glass ceramics according to the invention can be used in particular in the form of blanks in any shape and size, e.g. monolithic blanks or powder compacts, e.g. in unsintered, partially sintered or densely sintered form.

The machining is usually effected by material-removal processes and in particular by milling and/or grinding. It is particularly preferred that the machining is carried out as part of a CAD/CAM process. The glass according to the invention, the glass with nuclei according to the invention as well as the glass ceramic according to the invention can be used for the machining. The glasses and glass ceramics according to the invention can be used in particular in the form of blanks, e.g. monolithic blanks or powder compacts, e.g. in unsintered, partially sintered or densely sintered form. The glass ceramic according to the invention is preferably used for the machining. The glass ceramic according to the invention can also be used in a not fully crystallized form, which has been produced by heat treatment at a lower temperature. This offers the advantage that an easier machining and thus the use of simpler apparatus for the machining are possible. After the machining of such a partially crystallized material, the latter is regularly subjected to a further heat treatment in order to bring about further crystallization.

The glass ceramics according to the invention and the glasses according to the invention, in particular in the form of composites and combinations, are however also suitable as coating material for e.g. ceramics, glass ceramics and metals. The invention is therefore likewise directed towards the use of the glasses according to the invention or the glass ceramics according to the invention for coating in particular ceramics, glass ceramics and metals.

The invention also relates to a process for coating ceramics, glass ceramics and metals, in which glass ceramic according to the invention or glass according to the invention, in particular in the form of composites and combinations, is applied to the ceramic, the glass ceramic or the metal and exposed to a temperature of at least 600° C.

This can be effected in particular by sintering-on and preferably by pressing-on. In the case of sintering-on, the glass ceramic or the glass is applied in the usual way, e.g. as powder, to the material to be coated, such as ceramic, glass ceramic or metal, and then sintered. In the case of the preferred pressing-on, glass ceramic according to the invention or glass according to the invention is pressed on, e.g. in the form of powder compacts or monolithic blanks, at an increased temperature of e.g. from 700 to 1150° C. and in particular 700 to 1000° C., and with application of pressure, e.g. from 10 to 30 bar. For this, the methods described in EP 231 773 and the press furnace disclosed there can in particular be used. Suitable commercial furnaces are the Programat-type furnaces from Ivoclar Vivadent AG, Liechtenstein.

Because of the above-described properties of the glass ceramics according to the invention and the glasses according to the invention, these are suitable in particular for use in dentistry. A subject of the invention is therefore also the use of the glass ceramics according to the invention or the glasses according to the invention, in particular in the form of composites and combinations, as dental material and in particular for the preparation of dental restorations or as coating material for dental restorations, such as crowns, bridges and abutments.

The invention therefore also relates to a process for the preparation of a dental restoration, in particular an inlay, onlay, crown, partial crown, bridge, veneer, facet or abutment, in which the glass ceramic according to the invention or the glass according to the invention, in particular in the form of composites and combinations, is given the shape of the desired dental restoration by pressing, sintering or machining, in particular in a CAD/CAM process.

The invention is described in further detail in the following with reference to non-limitative examples.

EXAMPLES

A total of 21 glasses according to the invention were produced with the compositions specified in Table I, wherein the oxidation states of the specified oxides relate to the oxidation states of the raw materials used. The glasses were crystallized to form glass ceramics according to Table II. Herein, $T_g$ denotes glass transition temperature, determined by means of DSC $T_S$ and $t_S$ denote temperature and time used for melting $T_{Sinter}$ and $t_{Sinter}$ denote temperature and time used for sintering.

In addition, the glasses or glass ceramics according to Table III were mixed with further glasses and sintered to form glass ceramic bodies.

A) Preparation of Glasses According to the Invention

In the examples, starting glasses with the compositions specified in Table I were first melted on a scale of from 100 to 200 g from usual raw materials at the temperature $T_S$ for a duration $t_S$. Glass frits were produced by pouring the molten starting glasses into water. The fluorescence properties of the glass frits thus obtained at excitation wavelengths of 254, 366, 395 and 430 nm were determined visually by means of a UV lamp and are reproduced in Table II. According to this, all the glasses obtained in the examples exhibited a fluorescence, in particular at excitation wavelengths of 366, 395 and 430 nm.

The three method variants B) to D) specified below were used for the further processing of the glass frits:

B) Preparation of Glass Ceramics According to the Invention

In Examples 1 to 13, the glass frits obtained were ground to a grain size of <45 μm in a zirconium oxide mill. About 4 g of these powders were then pressed to form cylindrical blanks and, according to Table II, sintered at a temperature $T_{Sinter}$ and for a holding time of $t_{Sinter}$ to form dense glass ceramic bodies, wherein this was effected for sintering temperatures of up to 1200° C. in a vacuum in a Programat®-type sintering furnace (Ivoclar Vivadent AG), and for sintering temperatures above 1200° C. in a normal atmosphere in an LHT 02/16-type sintering furnace (Nabertherm). The fluorescence properties of the glass ceramics thus obtained at excitation wavelengths of 254, 366, 395 and 430 nm, respectively, were determined visually by means of a UV lamp and are reproduced in Table II. According to this, the glass ceramics obtained exhibited a fluorescence, in particular at excitation wavelengths of 366, 395 and 430 nm.

C) Glasses According to the Invention as Blending Components

The glass frits obtained in Examples 14 to 21 were comminuted and sieved to a grain size of <25 μm. The glass powders obtained were added to pulverized lithium silicate glasses according to Table III. In each case about 4 g of these mixtures were then pressed to form cylindrical or disc-shaped blanks and sintered in a sintering furnace (Programat® from Ivoclar Vivadent AG) to form dense glass ceramic bodies. The fluorescence properties of the glass ceramic bodies thus obtained at excitation wavelengths of 254, 366, 395 and 430 nm, respectively, were determined visually by means of a UV lamp and are reproduced in Table III. According to this, all the glass ceramic bodies obtained exhibited a fluorescence, in particular at excitation wavelengths of 366, 395 and 430 nm.

D) Glass Ceramics According to the Invention as Blending Components

The glass ceramics obtained in Examples 1, 2, 4 and 9 and the glass ceramic obtained after sintering at 1110° C. in Example 5 were comminuted and sieved to a grain size of <25 μm. The glass ceramic powders obtained were added to pulverized lithium silicate glasses according to Table III. In each case about 4 g of these mixtures were then pressed to form cylindrical or disc-shaped blanks or to form pressed stubs and sintered in a sintering furnace (Programat® from Ivoclar Vivadent AG) or hot-pressed to form dense glass ceramic bodies. The fluorescence properties of the glass ceramic bodies thus obtained at excitation wavelengths of 254, 366, 395 and 430 nm, respectively, were determined visually by means of a UV lamp and are reproduced in Table III. According to this, all the glass ceramic bodies obtained exhibited a fluorescence, in particular at excitation wavelengths of 366 nm. As crystal phases, calcium aluminosilicates such as anorthite were obtained in CaO-containing compositions, and strontium aluminosilicates such as slawsonite were obtained in SrO-containing compositions.

TABLE I

| Composition | 1 wt.-% | 2 wt.-% | 3 wt.-% | 4 wt.-% | 5 wt.-% | 6 wt.-% | 7 wt.-% | 8 wt.-% | 9 wt.-% | 10 wt.-% | 11 wt.-% |
|---|---|---|---|---|---|---|---|---|---|---|---|
| $SiO_2$ | 45.0 | 39.5 | 44.8 | 38.9 | 39.6 | 39.7 | 46.0 | 46.8 | 37.9 | 39.9 | 44.1 |
| $Al_2O_3$ | 37.3 | 32.7 | 37.1 | 32.3 | 33.0 | 33.0 | 34.3 | 31.0 | 31.4 | 33.1 | 36.7 |
| $Eu_2O_3$ | 0.7 | 0.7 | 0.7 | 0.7 | 0.7 | — | 0.8 | 0.8 | 2.5 | 0.1 | 0.7 |
| $Eu_2O_3$* | — | — | — | — | — | 0.6 | — | — | — | — | — |
| MgO | — | — | — | — | — | — | — | — | — | — | — |
| CaO | 16.4 | — | 16.3 | — | — | — | 18.9 | 21.4 | — | — | 16.1 |
| SrO | — | 26.6 | — | 26.2 | 26.7 | 26.7 | — | — | 25.5 | 26.9 | — |
| ZnO | — | — | — | — | — | — | — | — | — | — | — |
| SnO | 0.6 | 0.5 | 1.1 | 0.5 | — | — | — | — | — | — | — |
| $Li_2O$ | — | — | — | — | — | — | — | — | — | — | — |
| $Na_2O$ | — | — | — | — | — | — | — | — | — | — | — |
| $K_2O$ | — | — | — | — | — | — | — | — | — | — | — |
| $CeO_2$ | — | — | — | — | — | — | — | — | — | — | 2.4 |
| $ZrO_2$ | — | — | — | — | — | — | — | — | — | — | — |
| $Dy_2O_3$ | — | — | — | — | — | — | — | — | 2.7 | — | — |
| $Tb_4O_7$ | — | — | — | 1.4 | — | — | — | — | — | — | — |
| Σ | 100.0 | 100.0 | 100.0 | 100.0 | 100.0 | 100.0 | 100.0 | 100.0 | 100.0 | 100.0 | 100.0 |

| Composition | 12 wt.-% | 13 wt.-% | 14 wt.-% | 15 wt.-% | 16 wt.-% | 17 wt.-% | 18 wt.-% | 19 wt.-% | 20 wt.-% | 21** wt.-% |
|---|---|---|---|---|---|---|---|---|---|---|
| $SiO_2$ | 39.4 | 38.9 | 47.3 | 40.5 | 67.8 | 64.3 | 61.4 | 63.9 | 47.5 | 47.5 |
| $Al_2O_3$ | 32.7 | 32.3 | 39.2 | 33.6 | 26.0 | 24.7 | 23.5 | 18.3 | 39.3 | 39.3 |
| $Eu_2O_3$ | 1.3 | 2.6 | 0.8 | 0.7 | 0.8 | 0.8 | 0.7 | 0.8 | 0.8 | 0.8 |
| $Eu_2O_3$* | — | — | — | — | — | — | — | — | — | — |
| MgO | — | — | 12.4 | 10.6 | — | — | — | 4.5 | 12.4 | 12.4 |
| CaO | — | — | — | — | — | — | — | — | — | — |
| SrO | 26.6 | 26.2 | — | — | — | — | — | — | — | — |
| ZnO | — | — | — | — | — | — | — | 4.5 | — | — |
| SnO | — | — | 0.3 | 0.6 | 0.6 | 0.6 | 0.6 | 0.6 | — | — |
| $Li_2O$ | — | — | — | — | 4.8 | — | — | — | — | — |
| $Na_2O$ | — | — | — | — | — | 9.6 | — | — | — | — |
| $K_2O$ | — | — | — | — | — | — | 13.8 | — | — | — |
| $CeO_2$ | — | — | — | — | — | — | — | — | — | — |
| $ZrO_2$ | — | — | — | 14.0 | — | — | — | 7.4 | — | — |
| $Dy_2O_3$ | — | — | — | — | — | — | — | — | — | — |
| $Tb_4O_7$ | — | — | — | — | — | — | — | — | — | — |
| Σ | 100.0 | 100.0 | 100.0 | 100.0 | 100.0 | 100.0 | 100.0 | 100.0 | 100.0 | 100.0 |

*Used as europium(III) acetate hydrate
**Starting mixture for the glass melt contained 10 wt.-% sugar

TABLE II

| Example | 1 | 2 | 3 | 4 | 5 | 6 |
|---|---|---|---|---|---|---|
| $T_g$ [° C.] | 848 | 881 | 847 | 860 | 878 | 875 |
| $T_s$ [° C.] | 1600 | 1600 | 1650 | 1680 | 1650 | 1650 |
| $t_s$ [min] | 60 | 60 | 60 | 60 | 60 | 60 |
| Fluorescence glass 254 nm* | blue-white | yellowish-white | blue-white | white | light blue-white | light pink |
| Fluorescence glass 366 nm* | blue-white | yellowish white | blue-white | strong white | blue-white | blue-white |

TABLE II-continued

| | | | | | | | |
|---|---|---|---|---|---|---|---|
| Fluorescence glass 395 nm* | blue-white | yellowish white | | blue-white | white | blue-white | | yellowish white |
| Fluorescence glass 430 nm* | yellowish-white | yellowish white | | blue-white | white | yellowish-yellow | | yellowish-yellow |
| $T_{Sinter}$ [° C.] | 1140 | 1360 | 1500 | 1130 | 1360 | 1110 | 1360 | 1360 |
| $t_{Sinter}$ [min] | 60 | 60 | 60 | 60 | 60 | 60 | 60 | 60 |
| Fluorescence glass ceramic 254 nm* | pale blue-white | pale blue-white | | pale blue-white | blue-white | pale blue-white | pale blue-white | pale blue-white |
| Fluorescence glass ceramic 366 nm* | blue-white | strong blue-white | | strong blue-white | white | strong blue-white | strong blue-white | strong blue-white |
| Fluorescence glass ceramic 395 nm* | blue-white | white | | blue-white | blue-white | blue-white | blue-white | blue-white |
| Fluorescence glass ceramic 430 nm* | blue-white | white | | white | blue-white | | blue-white | blue-white |
| Crystal phase(s)** | CAS | SLA | | | | | | |

| Example | 7 | 8 | 9 | 10 | 11 | 12 | 13 |
|---|---|---|---|---|---|---|---|
| $T_g$ [° C.] | 846 | 833 | 860 | 871 | 852 | 847 | 867 |
| $T_s$ [° C.] | 1600 | 1600 | 1650 | 1650 + 1680 | 1600 | 1650 | 1650 |
| $t_s$ [min] | 60 | 60 | 60 | 45 + 15 | 60 | 60 | 60 |
| Fluorescence glass 254 nm* | light pink | pink | orange | blue-white | white | light pink | orange |
| Fluorescence glass 366 nm* | blue-white | blue-white | yellow | blue-white | blue-white | blue-white | yellowish |
| Fluorescence glass 395 nm* | yellowish white | yellowish white | orange | blue-white | light orange to pink | yellowish to greenish | yellow-orange |
| Fluorescence glass 430 nm* | light yellowish | light yellow | orange | blue-white | light orange to pink | yellowish to greenish | yellow-orange |
| $T_{Sinter}$ [° C.] | 1080 | 1150 | 1360 | 1360 | 1120 | 1400 | 1360 |
| $t_{Sinter}$ [min] | 60 | 60 | 60 | 60 | 60 | 720 | 60 |
| Fluorescence glass ceramic 254 nm* | | strong pink | blue-white | blue-white | blue-white | pale blue-white | blue |
| Fluorescence glass ceramic 366 nm* | strong blue-white | strong blue-white | blue-white | blue-white | blue-white | strong blue-white | strong blue |
| Fluorescence glass ceramic 395 nm* | blue-white | blue-white to pink | blue-white | blue-white | pale pink to pink | blue-white | blue |
| Fluorescence glass ceramic 430 nm* | pale white | pale pink | blue-white | blue-white | pink | white | blue |
| Crystal phase(s)** | AOT, CAS | AOT, CAS, WLT | | | | SLA, MLT | |

| Example | 14 | 15 | 16 | 17 | 18 | 19 | 20 | 21 |
|---|---|---|---|---|---|---|---|---|
| $T_g$ [° C.] | | 783 | | | | 751 | | |
| $T_s$ [° C.] | 1600 | 1650 | 1600 + 1650 + 1670 | 1650 + 1690 | 1690 | 1650 + 1690 | 1600 | 1600 |
| $t_s$ [min] | 60 | 60 | 60 + 60 + 15 | 60 + 40 | 60 | 45 + 60 | 60 | 15 |
| Fluorescence glass 254 nm* | blue-white | blue-white | blue-white | blue-white | blue-white | blue-white | blue-white | strong blue-white |
| Fluorescence glass 366 nm* | blue-white | blue-white | blue-white | blue-white | blue-white | blue-white | blue-white | strong blue-white |
| Fluorescence glass 395 nm* | blue-white | yellowish white | blue-white | blue-white | blue-white | yellowish white | blue-white | strong blue-white |
| Fluorescence glass 430 nm* | blue-white | yellowish white | blue-white | blue-white | blue-white | yellowish white | blue-white | strong blue-white |

*Fluorescence of the glass or of the glass ceramic at the specified excitation wavelength
**AOT: Anorthite (calcium aluminosilicate); CAS: calcium aluminosilicate; MLT: mullite (aluminium silicate); SLA: slawsonite (strontium calcium aluminosilicate); WLT: wollastonite (calcium silicate)

TABLE III

| Component A | % A** | Component B | % B** | Heat treatment | Fluorescence 254 nm* | Fluorescence 366 nm* | Fluorescence 395 nm* | Fluorescence 430 nm* |
|---|---|---|---|---|---|---|---|---|
| Glass according to Example 14 | 10 | Glass according to Example 10 of WO2016/120146A1 | 90 | Sintering 790° C./10 min (cylinder) | | blue-white | pale white | pale white |
| Glass according to Example 14 | 10 | Glass according to Example 31 of WO2017/055010A1 | 90 | Sintering 820° C./10 min (cylinder) | | blue-white | white | pale white |
| Glass according to Example 14 | 30 | Glass according to Example 31 of WO2017/055010A1 | 70 | Sintering 800° C./10 min (cylinder) | | blue-white | pale white | pale white |
| Glass according to Example 21 | 10 | Glass according to Example 3 of EP2377831A1 | 90 | Sintering 880° C./10 min (cylinder) | | green-yellow | pale white | pale white |
| Glass according to Example 21 | 10 | Glass according to Example 3 of EP2377831A1 | 90 | Sintering 900° C./10 min (disc) | | yellow-white | white | pale white |
| Glass according to Example 21 | 20 | Glass according to Example 3 of EP2377831A1 | 80 | Sintering 900° C./10 min (cylinder) | | pale yellow-white | pale yellow-white | light yellow |
| Glass ceramic according to Example 1 | 1 | Glass according to Example 9 of EP1688398A1 | 99 | Sintering 940° C./10 min (disc) | | blue-white | | |
| Glass ceramic according to Example 1 | 5 | Glass according to Example 9 of EP1688398A1 | 95 | Sintering 940° C./10 min (disc) | | light blue-white | | |
| Glass ceramic according to Example 1 | 5 | Glass according to Example 31 of WO2017/055010A1 | 95 | Sintering 900° C./10 min (disc) | | blue-white | blue-white | |
| Glass ceramic according to Example 1 | 5 | Glass according to WO2017/032745A1 | 95 | Sintering 830° C./60 min (cylinder) | light white | blue-white | blue-white | pale blue-white |
| Glass ceramic according to Example 2 | 1 | Glass according to WO2017/032745A1 | 99 | Sintering 820° C./60 min (disc) | | blue-white | pale blue-white | |
| Glass ceramic according to Example 2 | 5 | Glass according to WO2017/032745A1 | 95 | Sintering 820° C./60 min (disc) | pale blue-white | strong blue-white | blue-white | light blue-white |
| Glass ceramic according to Example 2 | 5 | Glass according to Example 3 of EP2377831A1 | 95 | Hot pressing 920° C./25 min (pressed stub) | | strong blue-white | pale blue-white | |
| Glass ceramic according to Example 2 | 5 | Glass according to Example 3 of EP2377831A1 | 95 | Sintering 900° C./10 min (disc) | light white | strong blue-white | pale blue-white | pale blue-white |
| Glass ceramic according to Example 2 | 10 | Glass according to Example 3 of EP2377831A1 | 90 | Sintering 900° C./10 min (disc) | light white | strong blue-white | blue-white | pale blue-white |
| Glass ceramic according to Example 2 | 10 | Glass according to Example 3 of EP2377831A1 | 90 | Sintering 890° C./10 min (cylinder) | blue-white | strong blue-white | blue-white | white |
| Glass ceramic according to Example 5 | 5 | Glass according to Example 3 of EP2377831A1 | 95 | Sintering 890° C./10 min (cylinder) | pale blue | strong blue | white | white |
| Glass ceramic according to Example 5 | 5 | Glass according to Example 3 of EP2377831A1 | 95 | Sintering 900° C./25 min (cylinder) | pale blue | strong blue-white | blue-white | pale blue |
| Glass ceramic according to Example 5 | 10 | Glass according to Example 3 of EP2377831A1 | 90 | Sintering 900° C./10 min (cylinder) | pale blue | strong blue-white | blue-white | light white |
| Glass ceramic according to Example 5 | 10 | Glass according to Example 3 of EP2377831A1 | 90 | Hot pressing 920° C./25 min (pressed stub) | pale blue | strong blue-white | blue-white | pale white |
| Glass ceramic according to Example 4 | 10 | Glass according to WO2017/032745A1 | 90 | Sintering 810° C./30 min (disc) | blue-white | strong blue-white | blue-white | blue-white |
| Glass ceramic according to Example 9 | 10 | Glass according to WO2017/032745A1 | 90 | Sintering 810° C./30 min (disc) | blue-white | strong blue-white | blue-white | blue-white |

*Fluorescence of the heat-treated body at the specified excitation wavelength;
**wt.-%

The invention claimed is:

1. Process for the preparation of a dental restoration, which process comprises giving a glass ceramic with europium content or a glass ceramic comprising the glass ceramic with europium content the shape of the desired dental restoration by pressing, sintering or machining, wherein the glass ceramic with europium content comprises the following components:

| Component | wt.-% |
| --- | --- |
| $SiO_2$ | 30.0 to 75.0 |
| $Al_2O_3$ | 15.0 to 45.0 |
| Europium, calculated as $Eu_2O_3$ | 0.05 to 5.0. |

2. Process according to claim 1 wherein the glass ceramic comprises 32.0 to 72.0 wt.-% $SiO_2$.

3. Process according to claim 1 wherein the glass ceramic comprises 15.0 to 40.0 wt.-% $Al_2O_3$.

4. Process according to claim 1 wherein the glass ceramic comprises 0.1 to 4.0 wt.-% europium, calculated as $Eu_2O_3$.

5. Process according to claim 1 wherein the glass ceramic comprises 8.0 to 30.0 wt.-% $Me^{II}O$, wherein $Me^{II}O$ is selected from MgO, CaO, SrO and ZnO.

6. Process according to claim 1 wherein the glass ceramic comprises 8.0 to 30.0 wt.-% oxide selected from CaO and SrO.

7. Process according to claim 1 wherein the glass ceramic comprises at least one of the following components in the specified amounts:

| Component | wt.-% |
| --- | --- |
| MgO | 0 to 13.0 |
| CaO | 0 to 22.0 |
| SrO | 0 to 28.0 |
| ZnO | 0 to 5.0. |

8. Process according to claim 1 wherein the glass ceramic comprises 0 to 10.0 wt.-% BaO.

9. Process according to claim 1 wherein the glass ceramic comprises 0 to 2.0 wt.-% tin, calculated as SnO.

10. Process according to claim 1 wherein the glass ceramic comprises 0 to 5.0 wt.-% cerium, calculated as $CeO_2$.

11. Process according to claim 1 wherein the glass ceramic comprises 0 to 3.0 wt.-% $B_2O_3$.

12. Process according to claim 1 wherein the glass ceramic comprises at least one of the following components in the specified amounts:

| Component | wt.-% |
| --- | --- |
| $SiO_2$ | 32.0 to 72.0 |
| $Al_2O_3$ | 15.0 to 40.0 |
| Europium, calculated as $Eu_2O_3$ | 0.1 to 4.0 |
| Cerium, calculated as $CeO_2$ | 0 to 5.0 |
| Tin, calculated as SnO | 0 to 2.0 |
| $Me^{I}_2O$ | 0 to 15.0 |
| $Me^{II}O$ | 0 to 30.0 |
| $Me^{III}_2O_3$ | 0 to 10.0 |
| $Me^{IV}O_2$ | 0 to 15.0 |
| $Me^{V}_2O_5$ | 0 to 6.0 |
| $Me^{VI}O_3$ | 0 to 6.0 |
| Fluorine | 0 to 5.0, | wherein
$Me^{I}_2O$ is selected from $Li_2O$, $Na_2O$, $K_2O$, $Rb_2O$ and $Cs_2O$,
$Me^{II}O$ is selected from MgO, CaO, SrO and ZnO,
$Me^{III}_2O_3$ is selected from $Y_2O_3$, $La_2O_3$, $Ga_2O_3$ and $In_2O_3$,
$Me^{IV}O_2$ is selected from $ZrO_2$ and $GeO_2$,
$Me^{V}_2O_5$ is selected from $P_2O_5$, $V_2O_5$, $Ta_2O_5$ and $Nb_2O_5$ and
$Me^{VI}O_3$ is selected from $WO_3$ and $MoO_3$.

13. Process according to claim 1 wherein the glass ceramic comprises at least one aluminosilicate as crystal phase.

14. Process according to claim 1 wherein the glass ceramic comprises at least 5 wt.-% aluminosilicate as crystal phase.

15. Process according to claim 1 further comprising a step in which a glass comprising the following components:

| Component | wt.-% |
| --- | --- |
| $SiO_2$ | 30.0 to 75.0 |
| $Al_2O_3$ | 10.0 to 45.0 |
| Europium, calculated as $Eu_2O_3$ | 0.05 to 5.0. | is subjected to at least one heat treatment at a temperature of from 1000 to 1500° C.

16. Process according to claim 1 wherein the glass ceramic is present in the form of a powder, a granulate or a blank.

17. Process according to claim 1 wherein the glass ceramic exhibit fluorescence at an excitation wavelength in the range of from 250 nm to 430 nm.

18. Process according to claim 15 wherein the glass comprises nuclei for the crystallization of an aluminosilicate.

19. Process according to claim 15, in which
(a) powder of the glass, optionally after the addition of further components, is pressed to form a powder compact, and
(b) the powder compact is subjected to a heat treatment at a temperature of from 1000 to 1500° C.

20. Process according to claim 1 comprising using the glass ceramic as blending component for setting the fluorescence of a glass or of a glass ceramic.

21. Process according to claim 1, wherein the dental restoration comprises an inlay, onlay, crown, partial crown, bridge, veneer, facet or abutment.

* * * * *